United States Patent [19]

Buchecker et al.

[11] Patent Number: 5,292,452
[45] Date of Patent: Mar. 8, 1994

[54] ALKENYLCYCLOHEXANE LIQUID CRYSTALLINE COMPOUNDS

[75] Inventors: Richard Buchecker, Zurich; Alfred Germann, Basel; Martin Schadt, Seltisberg; Alois Villiger, Basel, all of Switzerland

[73] Assignee: Hoffmann-La Roche Inc., Nutley, N.J.

[21] Appl. No.: 747,033

[22] Filed: Aug. 19, 1991

[30] Foreign Application Priority Data

Sep. 14, 1990 [CH] Switzerland ............... 2992/90
May 14, 1991 [CH] Switzerland ............... 1434/91

[51] Int. Cl.$^5$ .............. C09K 19/34; C09K 19/30; C07D 239/00; C07D 211/72
[52] U.S. Cl. .............. 252/299.61; 252/299.63; 252/299.01; 544/242; 546/346; 570/127; 570/182
[58] Field of Search .............. 544/335, 242; 546/346; 570/127, 182; 252/299.61, 299.63, 299.01

[56] References Cited

U.S. PATENT DOCUMENTS

| | | | |
|---|---|---|---|
| 4,676,604 | 6/1987 | Petrzilka | 252/299.6 |
| 4,770,503 | 9/1988 | Buchecker et al. | 252/299.61 |
| 4,877,547 | 10/1989 | Weber et al. | 252/299.61 |
| 4,886,621 | 12/1989 | Sage et al. | 252/299.61 |
| 4,917,819 | 4/1990 | Goto et al. | 252/299.63 |
| 5,013,477 | 5/1991 | Buchecker et al. | 252/299.63 |
| 5,055,224 | 10/1991 | Sage et al. | 252/299.63 |
| 5,122,295 | 6/1992 | Weber et al. | 252/299.63 |

FOREIGN PATENT DOCUMENTS

| | | |
|---|---|---|
| 122389 | 2/1984 | European Pat. Off. |
| 168683 | 6/1985 | European Pat. Off. |
| 315014 | 10/1988 | European Pat. Off. |
| 91/02709 | 3/1991 | World Int. Prop. O. |

OTHER PUBLICATIONS

Derwent Abstract of DE 4 025 550 No. 91-059126/09.

*Primary Examiner*—Philip Tucker
*Attorney, Agent, or Firm*—George M. Gould; George W. Johnston

[57] ABSTRACT

Compounds of the formula

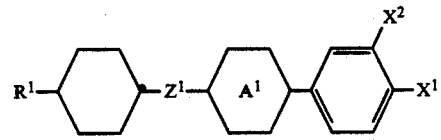

wherein $Z^1$ denotes a single covalent bond or —CH$_2$CH$_2$—; ring $A^1$ represents 1,4-phenylene, pyrimidine-2,5-diyl, pyridine-2,5-diyl or, when $Z^1$ stands for —CH$_2$CH$_2$—, also trans-1,4-cyclohexylene; $X^1$ stands for fluorine or chlorine; $X^2$ signifies fluorine, chlorine or hydrogen, with the proviso that $X^2$ only signifies hydrogen when $X^1$ is chlorine or when ring $A^1$ signifies pyridine-2,5-diyl and $Z^1$ signifies —CH$_2$CH$_2$—; and $R^1$ signifies 1E-alkenyl with 2 to 12 carbon atoms, their manufacture, liquid crystalline mixtures which contain these compounds and their use for electro-optical purposes.

16 Claims, No Drawings

ALKENYLCYCLOHEXANE LIQUID CRYSTALLINE COMPOUNDS

BACKGROUND

1. Field of the Invention

The present invention is concerned with halogenated three-ring alkenyl compounds, their manufacture, liquid crystalline mixtures which contain these compounds and their use for electro-optical purposes.

2. Description

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells having a twisted nematic structure, STN cells ("super-twisted nematic"), SBE cells ("super birefringence effect") and OMI cells ("optical mode interference"). The most common indicating devices are based on the Schadt-Helfrich effect and have twisted nematic structure.

The liquid crystal materials must have a good chemical and thermal stability and a good stability towards electric fields and electromagnetic radiation. Further, the liquid crystal materials should have low viscosity and in the cells should give short response times, low threshold potentials and a high contrast. Further, at the usual operating temperatures they should have a suitable mesophase, for example a nematic or cholesteric mesophase for the above-mentioned cells. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. In addition to the general interest in compounds having high optical anisotropy there has been an increased interest recently in materials having a low optical anisotropy, especially for actively addressed liquid crystals indicators, e.g. for TFT applications ("thin film transistor") in television sets, whereby, however, effects such as the occurrence of highly ordered smectic phases or an increase in the threshold potential and in the response times, which are frequently observed in the case of such materials, should be avoided as far as possible.

Since liquid crystals are usually used as mixtures of several components, it is important that the components have a good miscibility with one another.

SUMMARY OF THE INVENTION

The present invention provides compounds of the formula

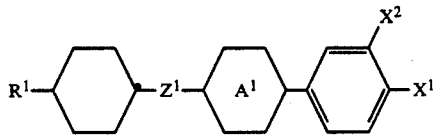

wherein $Z^1$ denotes a single covalent bond or —CH$_2$CH$_2$—; ring $A^1$ represents 1,4-phenylene, pyrimidine-2,5-diyl, pyridine-2,5-diyl or, when $Z^1$ stands for —CH$_2$CH$_2$—, also trans-1,4-cyclohexylene; $X^1$ stands for fluorine or chlorine; $X^2$ signifies fluorine, chlorine or hydrogen, with the proviso that $X^2$ only signifies hydrogen when $X^1$ is chlorine or when ring $A^1$ signifies pyridine-2,5-diyl and $Z^1$ signifies —CH$_2$CH$_2$—; and $R^1$ signifies 1E-alkenyl with 2 to 12 carbon atoms.

The compounds in accordance with the invention are liquid crystals having a broad nematic phase and a comparatively high clearing point. They have a surprisingly high dielectric anisotropy with a relatively low rotation viscosity and lead to a low threshold potential and short response times.

The compounds in accordance with the invention are suitable for indicating devices having a twisted nematic structure and TFT cells. By virtue of their good miscibility with one another and with known liquid crystal materials they can be used in a comparatively high concentration. They are especially suitable as components of nematic and cholesteric mixtures.

DETAILED DESCRIPTION OF THE INVENTION

The present invention pertains to compounds of the formula:

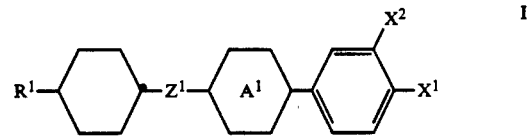

wherein $R^1$ is 1E-alkenyl of 2 to 12 carbon atoms; $Z^1$ is a single covalent bond or —CH$_2$CH$_2$—; ring $A^1$ is 1,4-phenylene, pyrimidin-2,5-diyl, pyridin-2,5-diyl, or when $Z^1$ is —CH$_2$CH$_2$—, $A^1$ also can be trans-1,4-cyclohexylene; $X^1$ is fluorine or chlorine; and $X^2$ is fluorine or chlorine; or when $X^1$ is chlorine, $X^2$ also can be hydrogen, and when ring $A^1$ is pyridin-2,5-diyl and $Z^1$ is —CH$_2$CH$_2$—, $X^2$ also can be hydrogen.

As used herein the term "1E-Alkenyl" embraces a straight-chain or branched alkyl group having a double bond in position 1. Straight-chain residues with 2 to 7 carbon atoms are generally preferred. Vinyl, 1E-propenyl, 1E-butenyl, 1E-pentenyl, 1E-hexenyl and 1E-heptenyl are especially preferred residues. Straight chain residues with 2 to 5 carbon atoms are particularly preferred.

The following formulae illustrate preferred compounds of formula I

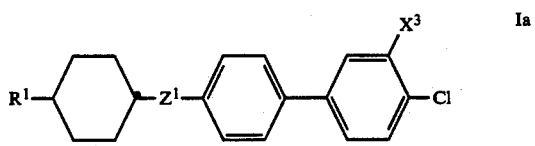

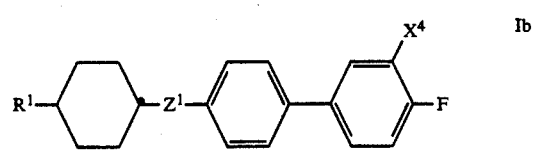

-continued

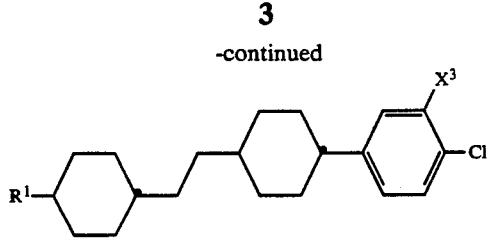   Ic

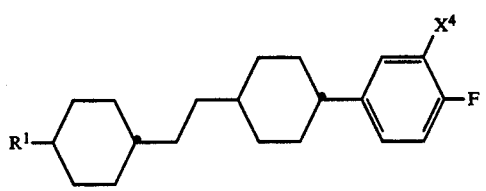   Id

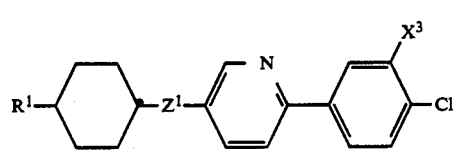   Ie

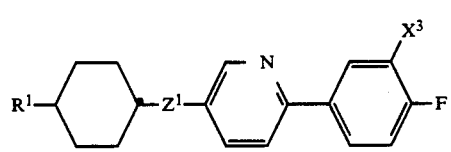   If

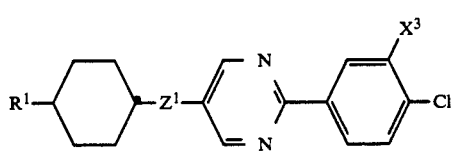   Ig

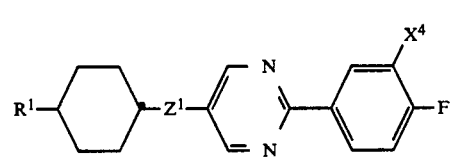   Ih wherein R1 and $Z^1$ are as defined for formula I; $X^3$ is fluorine, chlorine or hydrogen; and $X^4$ is fluorine or chlorine.

Especially preferred compounds of formulae Ia, Ib and Ie-h are those in which $Z^1$ is a single covalent bond.

The compounds of formulae Ia-If can be manufactured by reacting an aldehyde of the formula

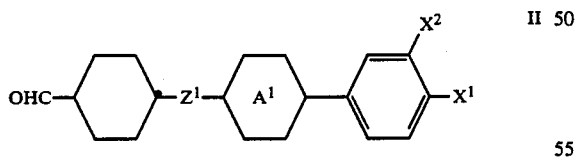   II wherein $Z^1$, $X^1$ and $X^2$ are as defined for formula I and ring $A^1$ is 1,4-phenylene, pyridine-2,5-diyl or, when $Z^1$ is for —CH$_2$CH$_2$—, ring $A^1$ also can be trans-1,4-cyclohexylene,
with a suitable alkyltriphenylphosphonium halide in the presence of a base.

The reaction with an alkyltriphenylphosphonium halide (especially with an alkyltriphenylphosphonium chloride, bromide or iodide) in the presence of a base can be effected in a manner known per se. Organic bases such as, for example, potassium tert.butylate, sodium methylate, sodium hydride, sodium amide and the like are suitable bases. The reaction is conveniently carried out in an inert organic solvent, for example an ether such as diethyl ether, tetrahyrofuran, dioxan or tert.butyl methyl ether. Temperature and pressure are not critical, but the reaction is generally carried out at atmospheric pressure and a temperature of 0° C. to the reflux temperature.

When R$^1$ is other than vinyl there are usually obtained E-/Z-isomeric mixtures which can be separated according to methods known per se, e.g. by chromatography on silica gel impregnated with silver nitrate. Further, if desired, the E/Z mixture or the Z-isomer can be converted predominantly into the E-form by equilibration with sulphinic acids, e.g. benzenesulphinic acid or p-toluenesulphinic acid.

The aldehydes of formula II can be prepared by methods known per se, for example according to the methods described in the Examples.

The compounds of formulae Ig and Ih can be prepared by the synthesis illustrated in Scheme 1. The preparation of compounds of general formula III is known and is described in EP-A-168683. The synthesis is carried out analogously to that described in Z. Naturf. 346, 1535 (1979) for structurally related compounds:

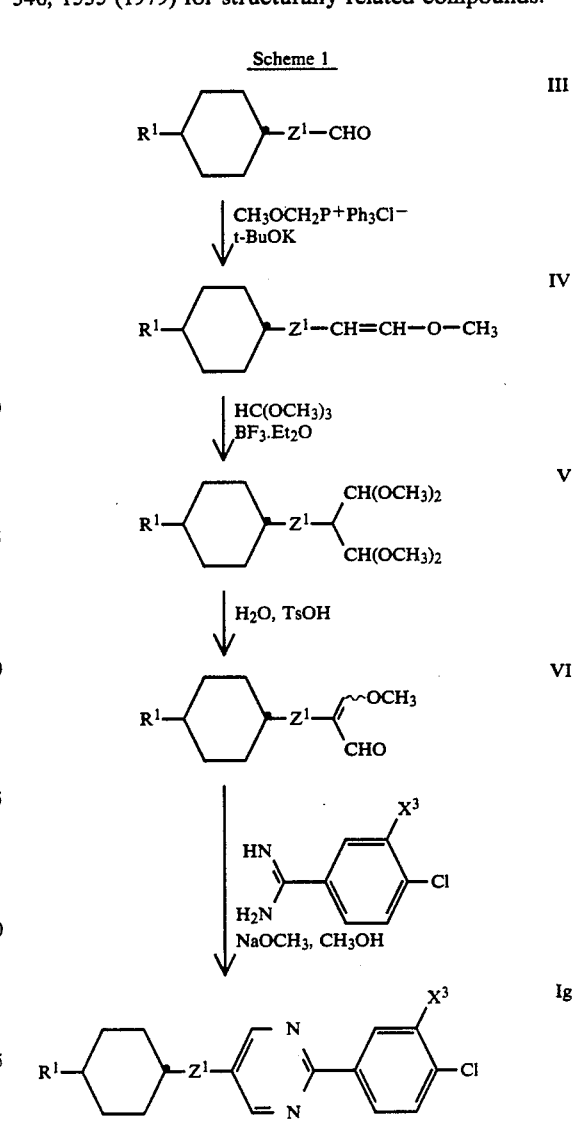

wherein $R^1$, $Z^1$ and $X^3$ have the definitions given above.

The compounds of formula I can be used in the form of mixtures with one another and/or with other liquid crystal components such as e.g. with substances from the classes of Schiff's bases, azobenzenes, azoxybenzenes, phenylbenzoates, cyclohexanecarboxylic acid phenyl esters, cyclohexanocarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and, moreover, many of them are commercially available.

The liquid crystalline mixtures in accordance with the invention contain at least two components, of which at least one component is a compound of formula I. A second component and optionally further components can be other compounds of formula I or other liquid crystal components. The compounds of formula I are especially suitable for nematic mixtures or, insofar as at least one component of the mixture is optically active, also for cholesteric mixtures.

Because of the good solubility of the compounds of formula I and their good miscibility with one another, their content in the mixtures in accordance with the invention can be relatively high. In general, however, a content of about 1–50 wt. %, especially about 5–30 wt. %, of the compounds of formula I is preferred.

The mixtures in accordance with the invention preferably contain, in addition to one or more compounds of formula I, one or more compounds from the group of compounds of the formulae

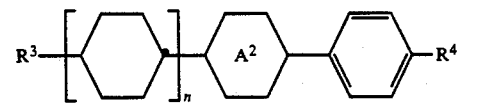

VII

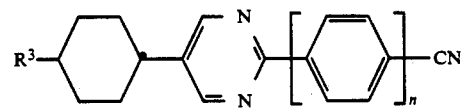

VIII

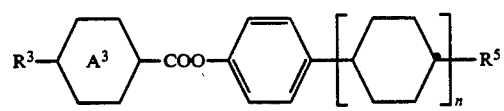

IX

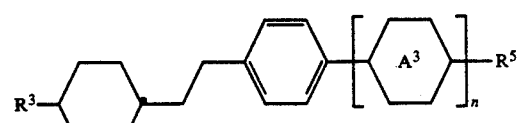

X

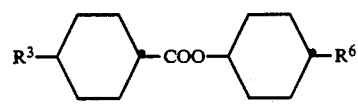

XI

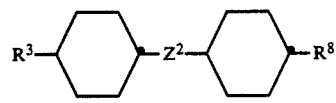

XII

-continued

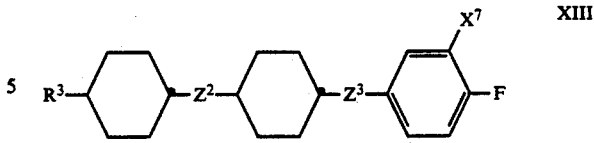

XIII

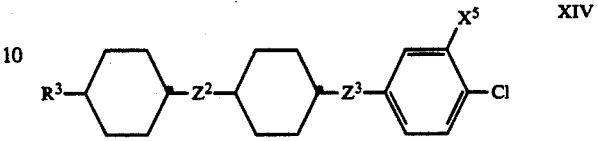

XIV

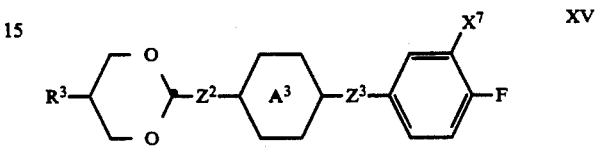

XV

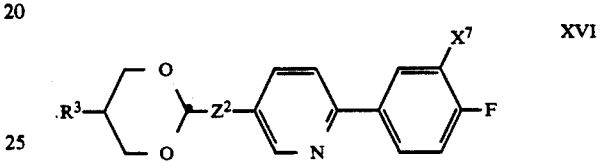

XVI

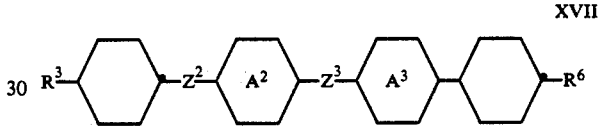

XVII

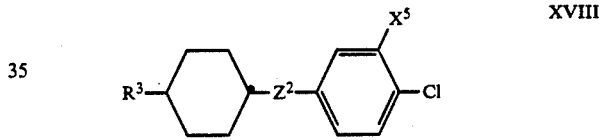

XVIII

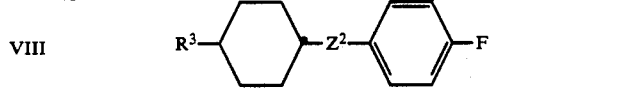

XIX

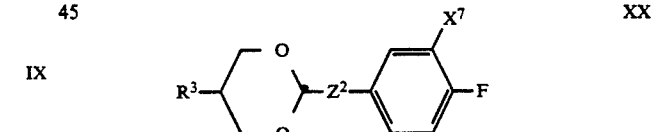

XX

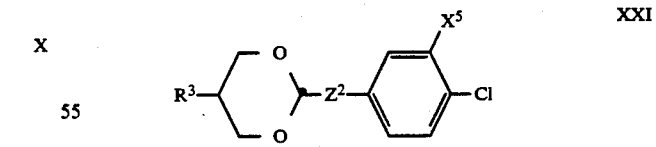

XXI

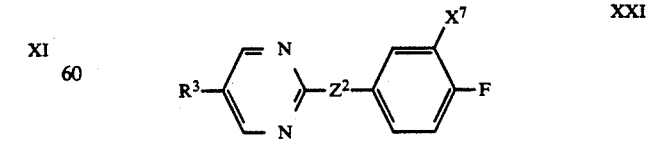

XXII

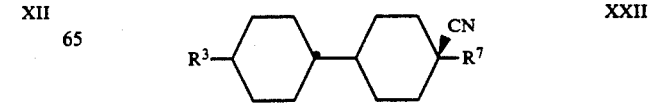

XXIII

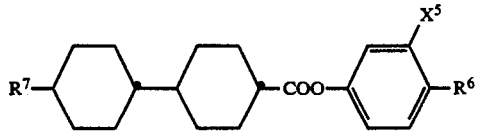

XXIV wherein n is either 0 or 1; $R^3$ and $R^6$ each independently are alkyl, 3E-alkenyl, 4-alkenyl, alkoxyalkyl or, when $R^3$ or $R^6$ are bonded to either trans-1,4-cyclohexylane or trans-1,3-dioxane-2,5-diyl, $R^3$ and $R^6$ also can be 1E-alkenyl; ring $A^2$ is 1,4-phenylene, trans-1,4-cyclohexylene, pyridine-2,5-diyl, pyrimidine-2,5-diyl or trans-1,3-dioxane-2,5-diyl; $R^4$ is cyano, -NCS, fluorine, alkyl, 3E-alkenyl, 4-alkenyl, alkoxy, 2E-alkenyloxy, 3-alkenyloxy or 1-alkynyl; ring $A^3$ is 1,4-phenylene or trans-1,4-cyclohexylene; $R^5$ is alkyl, 3E-alkenyl, 4-alkenyl or, when bonded to a trans-1,4-cyclohexylene ring, $R^5$ also can be 1E-alkenyl or, when $R^5$ is bonded to a 1,4-phenylene ring, $R^5$ also can be cyano, -NCS, alkoxy, 2E-alkenyloxy or 3-alkenyloxy; $R^7$ is alkyl, 1E-alkenyl, 3E-alkenyl or 4-alkenyl; $Z^2$ and $Z^3$ each individually are a single covalent bond or —$CH_2CH_2$—, with the proviso that two aromatic rings are always linked by a single covalent bond; $R^8$ is cyano, alkyl, 3E-alkenyl, 4-alkenyl, alkoxy, 2E-alkenyloxy, 3-alkenyloxy, alkoxymethyl, (2E-alkenyl)oxymethyl or when bonded to a trans-1,4-cyclohexylene ring, $R^8$ is also 1E-alkenyl; $X^5$ is hydrogen, chlorine or fluorine; $X^6$ is cyano, chlorine or fluorine; and $X^7$ is hydrogen or fluorine.

As used herein, the term "alkyl" embraces a straight-chain or branched alkyl group with 1–12 carbon atoms.

By the term "alkoxy" what is meant is the group —OJ—, wherein J is alkyl as defined hereinabove.

As used herein, the term "alkenyl" means a straight-chain or branched alkyl group having at least one double bond. Straight-chain residues with 2 to 7 carbon atoms are generally preferred. Straight-chain residues with 2 to 5 carbon atoms are particularly preferred.

By the term "alkenyloxy", what is meant is the group —O—Q wherein Q is an alkenyl as defined hereinabove.

As used herein, the term "alkoxyalkyl" means the group —J—O—J wherein J is an alkyl as defined hereinabove.

By the term "alkenyloxyalkyl" what is meant is the group —J—O—Q wherein J is an alkyl and Q is an alkenyl as defined above.

As used herein, "aromatic rings" includes, without limitation, substituted or unsubstituted 1,4-phenylene, pyridin-2,5-diyl, and pyrimidin-2,5-diyl.

By the term "1-alkynyl" what is meant is an alkyl as defined above having a triple bond in position 1.

Residues $R^3$ and $R^8$ each preferably have 1 to 12 carbon atoms, especially preferred are those with 1 to 7 carbon atoms. Straight-chain residues are generally preferred.

The production of the liquid crystalline mixtures and of the electro-optical devices can be effected in a manner known per se.

The invention is illustrated in more detail by the following Examples. In the Examples, C signifies a crystalline phase, S signifies a smectic phase, N signifies a nematic phase and I signifies the isotropic phase. $V_{10}$ denotes the voltage for 10% transmission. $t_{on}$ and $t_{off}$ denote respectively the switching-on time and the switching-off time. $\Delta n$ denotes the optical anisotropy.

Unless otherwise stated, the following examples were carried out as stated.

EXAMPLE 1 a) A suspension of 5.892 g of ethyltriphenylphosphonium bromide in 75 ml of tert.-butyl methyl ether was treated with 1.801 g of potassium tert.-butylate while stirring and gassing with nitrogen and stirred at room temperature for 1.5 hours. Subsequently, the suspension was treated dropwise at 2° C. within 45 minutes with a solution of 2.269 g of trans-4-(3',4'-difluoro-4-biphenylyl)cyclohexanecarboxaldehyde (prepared according to Example 3) in 17 ml of tert.-butyl methyl ether, stirred for a further 45 minutes and concentrated in a vacuum. The residue (9.7 g) was taken up in 50 ml of hexane, stirred and filtered. Concentration of the filtrate in a vacuum and chromatographical purification of the crude product obtained on silica gel with methylene chloride gave 2.464 g of 4-[trans-4-(propenyl)cyclohexyl]-3',4'-difluorobiphenyl (89.7% Z; 10.1% E).

b) A solution of 2.464 g of 4-[trans-4-(1-propenyl)cyclohexyl]-3',4'-difluorobiphenyl in 32 ml of toluene was treated with 2.4 ml of 3N hydrochloric acid and 0.375 g of sodium benzenesulphinate at room temperature while stirring and gassing with nitrogen, heated (oil bath temperature 60°–65° C.) for 4 hours, thereafter cooled to room temperature, treated with 100 ml of water and extracted twice with 150 ml of diethyl ether each time. The organic phase was washed once with 50 ml of 10 percent sodium hydrogen carbonate solution and once with 100 ml of 10 percent sodium chloride solution, dried over sodium sulphate and evaporated. The residue (2.78 g) was chromatographed with hexane and hexane/diethyl ether (1:1) on a silica gel column treated with silver nitrate and subsequently crystallized from hexane. This gave 1.195 g of 4-[trans-4-(1E-propenyl)-cyclohexyl]-3',4'-difluorobiphenyl as colourless crystals; m.p. (C-N) 97.7°–98.5° C., cl.p. (N-I) 134.2°–134.4° C.

The following compounds can be prepared in an analogous manner:

4-[trans-4-(1E-Butenyl)cyclohexyl]-3',4'-difluorobiphenyl, m.p. (C-N) 74.7° C., cl.p. (N-I) 120.3° C., 4-[trans-4-(1E-pentenyl)cyclohexyl]-3',4'-difluorobiphenyl, m.p. (C-N) 72.6° C., cl.p. (N-I) 124° C., 4-[trans-4-(1E-propenyl)cyclohexyl]-4'-chlorobiphenyl, m.p. (C-N) 174.5° C., cl.p. (N-I) 223.5° C., 4-[trans-4-(1E-Butenyl)cyclohexyl]-4'-chlorobiphenyl, 4-[trans-4-(1E-pentenyl)cyclohexyl]-4'-chlorobiphenyl, m.p. (C-N) 166.5° C., cl.p. (N-I) 214° C., 4-[trans-4-(1E-propenyl)cyclohexyl]-3'-fluoro-4'-chlorobiphenyl, m.p. (C-N) 122.4° C., cl.p. (N-I) 170.6° C., 4-[trans-4-(1E-butenyl)cyclohexyl]-3'-fluoro-4'-chlorobiphenyl, m.p. (C-N) 116.9° C., cl.p. (N-I) 159.3° C., 4-[trans-4-(1E-pentenyl)cyclohexyl]-3'-fluoro-4'-chlorobiphenyl, m.p. (C-N) 114° C., cl.p. (N-I) 159.8° C., 4-[trans-4-(1E-propenyl)cyclohexyl]-3'-chloro-4'-fluorobiphenyl, 4-[trans-4-(1E-propenyl)cyclohexyl]-3',4'-dichlorobiphenyl, 4-{2-[trans-4-(1E-propenyl)cyclohexyl]ethyl}-3',4'-difluorobiphenyl, 4-{2-[trans-4-(1E-butenyl)cyclohexyl]ethyl}-3',4'-difluorobiphenyl, 4-{2-[trans-4-(1E-pentenyl)cyclohexyl]ethyl}-3',4'-difluorobiphenyl, 4-{2-[trans-4-(1E-propenyl)cyclohexyl]ethyl}-4'-chlorobiphenyl, 4-{2-[trans-4-(1E-butenyl)cyclohexyl]ethyl}-4'-chlorobiphenyl, 4-{2-[trans-4-(1E-pentenyl)cyclohexyl]ethyl}-4'-chlorobiphenyl, 4-{2-[trans-4-(1E-propenyl)cyclohexyl]ethyl}-3'-fluoro-4'-chlorobiphenyl, 4-{2-[trans-4-(1E-butenyl)cyclohexyl]ethyl}-3'-fluoro-4'-chlorobiphenyl, 4-{2-[trans-4-(1E-pentenyl)cyclohexyl]ethyl}-3'-fluoro-4'-chlorobiphenyl, 4-{2-[trans-4-(1E-propenyl)cyclohexyl]ethyl}-3'-chloro-4'-fluorobiphenyl, 4-{2-[trans-4-(1E-propenyl)cyclohexyl]ethyl}-3',4'-dichlorobiphenyl, 1-{trans-4-[2-[trans-4-(1E-propenyl)cyclohexyl]ethyl]-cyclohexyl}-3,4-difluorobenzene, 1-{trans-4-[2-[trans-4-(1E-butenyl)cyclohexyl]ethyl]-cyclohexyl}-3,4-difluorobenzene, 1-{trans-4-[2-[trans-4-(1E-pentenyl)cyclohexyl]ethyl]-cyclohexyl}-3,4-difluorobenzene, 1-{trans-4-[2-[trans-4-(1E-propenyl)cyclohexyl]ethyl]-cyclohexyl}-4-chlorobenzene, 1-{trans-4-[2-[trans-4-(1E-butenyl)cyclohexyl]ethyl]-cyclohexyl}-4-chlorobenzene, 1-{trans-4-[2-[trans-4-(1E-pentenyl)cyclohexyl]ethyl]-cyclohexyl}-4-chlorobenzene, 1-{trans-4-[2-[trans-4-(1E-propenyl)cyclohexyl]ethyl]-cyclohexyl}-3-fluoro-4-chlorobenzene, 1-{trans-4-[2-[trans-4-(1E-butenyl)cyclohexyl]ethyl]-cyclohexyl}-3-fluoro-4-chlorobenzene, 1-{trans-4-[2-[trans-4-(1E-pentenyl)cyclohexyl]ethyl]-cyclohexyl}-3-fluoro-4-chlorobenzene, 1-{trans-4-[2-[trans-4-(1E-propenyl)cyclohexyl]ethyl]-cyclohexyl}-3-chloro-4-chlorobenzene, 1-{trans-4-[2-[trans-4-(1E-propenyl)cyclohexyl]ethyl]-cyclohexyl}-3,4-dichlorobenzene, 2-(3,4-difluorophenyl)-5-[trans-4-(1E-propenyl)cyclohexyl}pyridine, 2-(3,4-difluorophenyl)-5-[trans-4-(1E-butenyl)cyclohexyl}pyridine, 2-(3,4-difluorophenyl)-5-[trans-4-(1E-pentenyl)cyclohexyl}pyridine, 2-(4-chlorophenyl)-5-[trans-4-(1E-propenyl)cyclohexyl}pyridine, 2-(4-chlorophenyl)-5-[trans-4-(1E-butenyl)cyclohexyl}pyridine, 2-(4-chlorophenyl)-5-[trans-4-(1E-pentenyl)cyclohexyl}pyridine, 2-(3-fluoro-4-chlorophenyl)-5-[trans-4-(1E-propenyl)cyclohexyl]pyridine, 2-(3-fluoro-4-chlorophenyl)-5-[trans-4-(1E-butenyl)-cyclohexyl]pyridine, 2-(3-fluoro-4-chlorophenyl)-5-[trans-4-(1E-pentenyl)-cyclohexyl]pyridine, 2-(3-chloro-4-fluorophenyl)-5-[trans-4-(1E-propenyl)cyclohexyl]pyridine, 2-(3,4-dichlorophenyl-5-[trans-4-(1E-propenyl)-cyclohexyl]pyridine, 2-(3,4-difluorophenyl)-5-[2-[trans-4-(1E-propenyl)cyclohexyl]ethyl]pyridine, m.p. (C-N) 80.4° C., cl.p.(N-I) 112.8° C., 2-(3,4-difluorophenyl)-5-[2-[trans-4-(1E-butenyl)cyclohexyl]ethyl]pyridine, 2-(3,4-difluorophenyl)-5-[2-[trans-4-(1E-pentenyl)cyclohexyl]ethyl]pyridine, 2-[2-(4-chlorophenyl)ethyl]-5-[trans-4-(1E-propenyl)-cyclohexyl]pyridine, m.p. (C-N) 137.7° C., $S_A$-N 83.7° C., cl.p. (N-I) 179.5° C., 2-(4-chlorophenyl)-5-[2-[trans-4-(1E-butenyl)-cyclohexyl]ethyl]pyridine, 2-(4-chlorophenyl)-5-[2-[trans-4-(1E-pentenyl)-cyclohexyl]ethyl]pyridine, 2-(3-fluoro-4-chlorophenyl)-5-[2-[trans-4-(1E-propenyl)cyclohexyl]ethyl]pyridine, 2-(3-fluoro-4-chlorophenyl)-5-[2-[trans-4-(1E-butenyl)cyclohexyl]ethyl]pyridine, 2-(3-fluoro-4-chlorophenyl)-5-[2-[trans-4-(1E-pentenyl)cyclohexyl]ethyl]pyridine, 2-(3-chloro-4-fluorophenyl)-5-[2-[trans-4-(1E-propenyl)cyclohexyl]ethyl]pyridine, 2-(3,4-dichlorophenyl)-5-[2-[trans-4-(1E-propenyl)-cyclohexyl]ethyl]pyridine, 2-(4-fluorophenyl)-5-[2-[trans-4-(1E-propenyl)cyclohexyl]ethyl]pyridine, m.p. (C-N) 98° C., cl.p. (N-I) 144° C., 2-(4-fluorophenyl)-5-[2-[trans-4-(1E-butenyl)cyclohexyl]ethyl]pyridine, m.p. (C-N) 98.1° C., cl.p. (N-I) 134.4° C., 2-(4-fluorophenyl)-5-[2-[trans-4-(1E-pentenyl)cyclohexyl]ethyl]pyridine.

EXAMPLE 2

A suspension of 0.977 g of methyltriphenylphosphonium bromide in 12 ml of tert.-butyl methyl ether was treated with 0.308 g of potassium tert.-butylate while stirring and gassing with nitrogen and stirred at room temperature for a further 1.5 hours. The yellow suspension was treated dropwise at 2° C. within 15 minutes with a solution of 0.439 g of trans-4-(3',4'-difluoro-4-biphenylyl)cyclohexanecarboxaldehyde in 12 ml of tert.-butyl methyl ether, stirred at room temperature for a further 1.5 hours and concentrated in a vacuum. Purification of the residue by chomatography on silica gel with methylene chloride and subsequent two-fold recrystallization from hexane gave 0.118 g of pure 4-(trans-4-vinylcyclohexyl)-3',4'-difluorobiphenyl; m.p. (C-N) 97.0° C., cl.p. (N-I) 84.7° C.

The following compounds can be prepared in an analogous manner:

4-(trans-4-vinylcyclohexyl)-4'-chlorobiphenyl, m.p. (C-N) 165.2° C., cl.p. (N-I) 183.4° C., 4-(trans-4-vinylcyclohexyl)-4'-chloro-3'-fluorobiphenyl, m.p. (C-N) 121.9° C., cl.p. (N-I) 125.3° C., 4-(trans-4-vinylcyclohexyl)-3',4'-dichlorobiphenyl, 4-(trans-4-vinylcyclohexyl)-3'-chloro-4'-fluorobiphenyl, 4-[2-(trans-4-vinylcyclohexyl)ethyl]-3',4'-difluorobiphenyl, 4-[2-(trans-4-vinylcyclohexyl)ethyl]-4'-chlorobiphenyl, 4-[2-(trans-4-vinylcyclohexyl)ethyl]-3'-fluoro-4'-chlorobiphenyl, 1-{trans-4-vinylcyclohexyl)ethyl]cyclohexyl}-3,4-difluorobenzene, 1-{trans-4-vinylcyclohexyl)ethyl]cyclohexyl}-4-chlorobenzene, 1-{trans-4-vinylcyclohexyl)ethyl]cyclohexyl}-3-fluoro-4-chlorobenzene, 2-(3,4-difluorophenyl)-5-(trans-4-vinylcyclohexyl)-pyridine, 2-(4-chlorophenyl)-5-(trans-4-vinylcyclohexyl)pyridine, 2-(3-fluoro-4-chlorophenyl)-5-(trans-4-vinylcyclohexyl)pyridine, 2-(3,4-dichlorophenyl)-5-(trans-4-vinylcyclohexyl)-pyridine, 2-(4-fluorophenyl)-5-[2-(trans-4-vinylcyclohexyl)ethyl]pyridine, m.p. (C-N) 72° C., cl.p. (N-I) 113.3° C., 2-(3,4-difluorophenyl)-5[2-(trans-4-vinylcyclohexyl)ethyl]pyridine, m.p. (C-N) 67.7° C., cl.p. (N-I) 80.2° C., 2-(4-chlorophenyl)-5-[2-(trans-4-vinylcyclohexyl)ethyl]pyridine, m.p. (C-N) 99.9° C., $S_A$-N 76.7° C., cl.p. 148.7° C., 2-(3-fluoro-4-chlorophenyl)-5-[2-(trans-4-vinylcyclohexyl)ethyl]pyridine, 2-(3-chloro-4-fluorophenyl-5-[2-(trans-4-vinylcyclohexyl)ethyl]pyridine, 2-(3,4-dichlorophenyl)-5-[2-(trans-4-vinylcyclohexyl)ethyl]pyridine.

The aldehydes used as the starting materials in Examples 1 and 2 can be prepared as described in Examples 3 to 6.

EXAMPLE 3 a) A suspension of 109.6 g of 4-(4-nitrophenyl)cyclohexanone (preparable by nitrating 4-phenylcyclohexanone) in 1 l of dioxan was treated with 50 ml of triethylamine and 2 g of 5 percent palladium/carbon and hydrogenated at room temperature and 0.3 bar hydrogen pressure while stirring well. The mixture was filtered after 2 hours. The filtrate was evaporated in a water-jet vacuum at a bath temperature of 30° C. and the evaporation residue was dried at 40° C. overnight in a drying oven under a water-jet vacuum. There were thus obtained 94.5 g of 4-(4-aminophenyl)cyclohexanone as white crystals with m.p. 127°-128° C.

b) 200 ml of 4N sulphuric acid were heated to 80° C. in a sulphonation flask and then treated with about 5% of a solution of 37.9 g of 4-(4-aminophenyl)cyclohexanone in 200 ml of 4N sulphuric acid. Subsequently, the remaining solution of 4-(4-aminophenyl)cyclohexanone as well as a solution of 15.2 g of sodium nitrite in 45 ml of water were simultaneously added dropwise to the reaction mixture at 80° C. within 1.5 hours. Thereafter, the mixture was treated dropwise at 80° C. within 30 minutes with a solution of 9 g of sodium nitrite in 27 ml of water and stirred at 80° C. for a further 1 hour. After cooling the reaction mixture to 0° C. the separated crystals were filtered off under suction, washed with 200 ml of cold water and dried up to constant weight at 60° C. in a drying oven under a water-jet vacuum. The crystalline crude product (34.6 g) was suspended in 520 ml of ethyl acetate. The suspension was heated to reflux for 1 hour, treated with 1.7 g of active charcoal and then heated to reflux for a further 1 hour. Subsequently, the mixture was suction filtered (rinsing with 40 ml of warm ethyl acetate) and the filtrate was evaporated in a water-jet vacuum at a bath temperature of 40° C. Drying of the evaporation residue in a water-jet vacuum at 60° C. up to constant weight gave 32.2 g of 4-(4-hydroxyphenyl)cyclohexanone as yellow-brown crystals with m.p. 165°-166° C.

c) A suspension of 13.7 g of 4-(4-hydroxyphenyl)cyclohexanone in 350 ml of ethylene chloride was heated to reflux for 3 hours with 11.6 ml of ethylene glycol and 1.6 g of Amberlyst ® 15 (strongly acidic ion exchang resin, Fluka AG) while stirring and separating water. Thereafter, the brown reaction solution was cooled to room temperature and washed twice with 200 ml of water each time. The aqueous phases were backextracted with 200 ml of methylene chloride. The organic phases were dried over sodium sulphate, filtered and concentrated on a rotary evaporator. The brown crystals obtained (17.4 g) were dissolved in 50 ml of hot ethyl acetate. The solution was treated with 50 ml of hexane and left to crystallize in a water bath. The precipitate was filtered off under suction and dried at 50° C., there being obtained 12.4 g of crude product as brown crystals. Working-up of the mother liquor gave a further 4.8 g of crude product. The crude product was purified by chromatography on silica gel with methylene chloride/acetone (volume ratio firstly 97:3, then 95:5) at 0.4 bar. Recrystallization of the orange, crystalline product from ethyl acetate/hexane (vol. 1:2) gave 15.0 g of 4-(1,4-dioxa-8-spiro[4.5]decyl)phenol as yellow-orange crystals with m.p. 151.7°-152.6° C.

d) A suspension of 13.0 g of 4-(1,4-dioxa-8-spiro[4.5]decyl)phenol in 150 ml of methylene chloride was treated with 7.6 ml of 2,6-lutidine, whereby the precipitate passed into solution. The orange solution was cooled to 0° C. and treated dropwise within 15 minutes at 0°-2° C. with a solution of 10.9 ml of trifluoromethanesulphonic anhydride in 80 ml of methylene chloride. The reaction mixture was stirred at 0°-2° C. for a further 30 minutes and then treated dropwise with 100 ml of water at 0°-5° C. within 5 minutes. Subsequently, the organic phase was washed with 100 ml of about 10 percent copper sulphate solution. The aqueous phases were extracted with 100 ml of methylene chloride. The organic phases were dried over sodium sulphate, filtered and concentrated on a rotary evaporator. The brownish oil obtained (20.1 g) was purified by chromatography on silica gel with methylene chloride at 0.4 bar. There were thus obtained 9.7 g of 4-(1,4-dioxaspiro[4,5]decyl)phenyl trifluoromethanesulphonate as a brownish, crystallizing oil. Further fractions gave 9.2 g of a brownish oil (consisting of 70% of the desired ketal and 30% of the corresponding ketone) which was not worked-up.

e) A mixture of 0.399 g of magnesium shavings, a granule of iodine and 10 ml of diethyl ether was treated dropwise within 15 minutes with a solution of 1.88 ml of 3,4-difluoro-1-bromobenzene in 20 ml of diethyl ether while stirring and gassing with nitrogen. The mixture was warmed slightly and the stirred at reflux for 15 minutes. The Grignard reagent solution obtained was cooled to room terperature and filtered. A mixture of 2.0 g of 4-(1,4-dioxaspiro[4,5]decyl)phenyl trifluoromethanesulphonate, 20 ml of tetraydrofuran and 0.5 g of tetrakis(triphenylphosphine)palladium was heated to 60°-65° C. while stirring and gassing with nitrogen and treated dropwise within 4 hours with the Grignard reagent solution. The reaction mixture was subsequently stirred at 60°-65° C. for a further 2.5 hours, during this time the ether was replaced by 10 ml of tetrahydrofuran, the dark solution was stirred at 65°-67° C. for 18 hours, cooled to 10°-15° C., treated cautiously with 30 ml of water and then dropwise with 5 ml of 3N hydrochloric acid. The mixture was extracted twice with 100 ml of diethyl ether each time. The ether phases were washed with 100 ml of 10 percent sodium hydrogen carbonate solution and with 100 ml of 10 percent sodium chloride solution, dried over sodium sulphate, filtered and, after concentration of the filtrate, gave 3.13 g of crude 4-(1,4-dioxa-8-spiro[4,5]-decyl)-3',4'-difluorobiphenyl. Purification by chromatography on silica gel with ethyl acetate/hexane (1:9) yielded 1.5 g of brownish crystals.

f) A solution of 1.5 g of 4-(1,4-dioxa-8-spiro[4,5]-decyl)-3',4'-difluorobiphenyl in 50 ml of toluene was stirred with 15 ml of formic acid at room temperature for 1 hour, treated with 100 ml of water and extracted twice with 100 ml of diethyl ether each time. The organic phases were combined, washed once with 100 ml of 10 percent sodium hydrogen carbonate solution and once with 100 ml of 10 percent sodium chloride solution, dried over sodium sulphate and, after evaporation, gave 1.402 g of a brownish residue. Purification of the residue by chromatography on 60 g of silica gel with methylene chloride gave 1.307 g of 4-(3',4'-difluoro-4-biphenylyl)-cyclohexanone as brownish crystals which gave 1.038 g of colourless crystals after recrystallization from methylene chloride/hexane.

g) A suspension of 5.707 g of dry (methoxymethyl)triphenylphosphonium chloride in 35 ml of tert.-butyl methyl ether, gassed with nitrogen, was treated with 1.953 g of potassium tert.-butylate while stirring at −15° C., stirred for 30 minutes and warmed to −5° C. 3.185 g of 4-(3',4'-difluoro-4-biphenylyl)cyclohexanone in 20 ml of tetrahydrofuran (absolute) and 10 ml of tert.-butyl methyl ether were added dropwise to the orange suspension within 10 minutes, the cooling bath was removed, the reaction mixture was stirred at room temperature for 1.5 hours, diluted with 50 ml of hexane, filtered and the filter residue was washed with hexane. The filtrate gave 6.2 g of brown oily crystals after evaporation. The filter residue was taken up in 25 ml of methylene chloride and 50 ml of hexane. This filtrate gave a further 1.8 g of product as brown oily crystals. The product (6.2 and 1.8 g) gave, after purification by chromatography on 120 g of silica gel at a pressure of 0.5 bar with methylene chloride, 3.552 g of 4-[(methoxymethylidene)cyclohexyl]-3',4'-difluorobiphenyl as a colourless oil.

h) A mixture of 3.552 g of 4-[(methoxymethylidene)-cyclohexyl]-3',4'-difluorobiphenyl in 18 ml of tetrahydrofuran and 4.5 ml of 2N hydrochloric acid was heated to boiling for 30 minutes while gassing with nitrogen, cooled, treated with 150 ml of water and extracted twice with 100 ml of methylene chloride each time. The organic phases were combined, washed with 100 ml of 10 percent sodium chloride solution, dried over sodium sulphate and evaporated. This gave 3.418 g of a cis-/trans mixture of 4-(4-formylcyclohexyl)-3',4'-difluorobiphenyl (15.1% cis/84.8% trans) which was dissolved in 80 ml of methanol and 8 ml of methylene chloride and stirred under nitrogen for 30 minutes with 3 drops of triethylamine and 1.6 ml of 20 percent sodium hydroxide solution (g/g). The yellowish solution was treated with 150 ml of water and extracted twice with 100 ml of methylene chloride each time. The organic phase was washed with 100 ml of 10 percent sodium chloride solution, dried over sodium sulphate and, after evaporation, gave 3.398 g of a colourless oil which, after purification by chromatography on 120 g of silica gel at a pressure of 0.5 bar with hexane/ethyl acetate (9:1) and subsequent crystallisation from methylene chloride/hexane at 0° C., yielded 2.629 g of pure trans-4-(3',4'-difluoro-4-biphenylyl)cyclohexanecarboxaldehyde.

The following compounds can be prepared in an analogous manner:

trans-4-(4'-Chloro-4-biphenylyl)carboxaldehyde,
trans-4-(3',4'-dichloro-4-biphenylyl)carboxaldehyde,
trans-4-(3'-chloro-4'-fluoro-4-biphenylyl)carboxaldehyde,
trans-4-(4'-chloro-3'-fluoro-4-biphenylyl)carboxaldehyde.

EXAMPLE 4 a) 4.53 g of magnesium shavings and a granule of iodine are treated with 150 ml of tetrahydrofuran while stirring and gassing with nitrogen. Subsequently, the mixture is treated dropwise within 20 minutes with a solution of 38.4 g of 1-bromo-4-chlorobenzene in 150 ml of tetrahydrofuran and boiled at reflux for 1.25 hours. Thereafter, the reaction mixture is cooled to 0° C. and treated dropwise at 0°-5° C. within 30 minutes with a solution of 35.7 g of 8-[2-(4-oxocyclohexyl)ethyl]-1,4-dioxaspiro[4,5]decane (prepared starting from 4,4'-(1,2-ethane-diyl)bisphenol in analogy to the synthesis of 8-(4-oxocyclohexyl)-1,4-dioxaspiro[4,5]decane described in EP-A-310,067) in 240 ml of tetrahydrofuran. The reaction mixture is stirred without cooling for a further 4 hours, then treated within 10 minutes with 240 ml of 10 percent ammonium chloride solution and extracted with diethyl ether. The ether phases are washed with water, dried over sodium sulphate, filtered and concentrated, there being obtained 1-(4-chlorophenyl)-4-[2-(1,4-dioxa-spiro[4,5]decyl)ethyl]cyclohexanol.

b) A solution of 54.7 g of 1-(4-chlorophenyl)-4-[2-(1,4-dioxaspiro[4.5]decyl)ethyl]cyclohexanol in 570 ml of ethylene chloride is treated with 6.95 ml of ethylene glycol and 6.95 g of Amberlyst ® 15 (strongly acidic ion exchange resin, Fluka AG) and refluxed through neutral aluminium oxide for 2.3 hours. There-after, the reaction mixture is cooled to room temperature, filtered and washed with water. The aqueous phases are extracted with methylene chloride. The organic phases are dried over sodium sulphate, filtered and concentrated. The crude product obtained is dissolved in 150 ml of ethyl acetate. The solution is treated with active charcoal and filtered while hot. The filtrate is partially evaporated, then treated with methanol and stored at room temperature. There is thus obtained 4-chloro-1-[4-(2-(1,4-dioxa-8-spiro[4.5]decyl)ethyl)-1-cyclohexenyl]-benzene as a colourless precipitate.

c) A solution of 35.0 g of 4-chloro-1-[4-(2-(1,4-dioxa-8-spiro[4.5]decyl)ethyl)-1-cyclohexenyl]benzene in 1 l of toluene is treated with 2.6 g of palladium/carbon (10%) and hydrogenated at room temperature under normal pressure until the uptake of hydrogen comes to a standstill. Thereafter, the reaction mixture is filtered and the filtrate is concentrated, there being obtained crude 4-chloro-1-[4-(2-(1,4-dioxa-8-spiro[4.5]decyl)ethyl)cyclohexyl]benzene. A suspension of 32.8 g of aluminium chloride in 215 ml of methylene chloride is treated at 18° C. while stirring and gassing with nitrogen within 10 minutes with a solution of the crude product obtained in 110 ml of methylene chloride and stirred at 0° C. for a further 30 minutes. Subsequently, the reaction mixture is poured on to 600 ml of ice/water, stirred for 10 minutes and then extracted three times with methylene chloride. The organic phases are washed in succession with water, with saturated sodium hydrogen carbonate solution and with water, then dried over sodium sulphate and filtered. Concentration of the filtrate gives 4-chloro-1-[trans-4-[2-(1,4-dioxa-8-spiro[4.5]decyl)ethyl]cyclohexyl]benzene.

d) A mixture of 31.1 g of 4-chloro-1-[trans-4-[2-(1,4-dioxa-8-spiro[4.5]decyl)ethyl]cyclohexyl]benzene, 207 ml of toluene and 103 ml of formic acid is stirred at room temperature for 1.25 hours while gassing with nitrogen. Thereafter, the reaction mixture is poured into 500 ml of water and extracted with methylene chloride. The organic phases are washed with saturated sodium hydrogen carbonate solution and with water, dried over sodium sulphate and filtered. Concentration of the filtrate gives 4-[2-[trans-4-(4-chlorophenyl)cyclohexyl]ethyl]cyclohexanone.

e) A suspension of 35.5 g of (methoxymethyl)triphenylphosphonium chloride in 210 ml of tert.-butyl methyl ether is treated with 12.2 g of potassium tert.-butylate at −15° C. while stirring and gassing with nitrogen. The suspension is stirred at 5° C. for a further 30 minutes, then treated dropwise at 0°-5° C. within 40 minutes with a solution of 20 g of 4-[2-[trans-4-(4-chlorophenyl)cyclohexyl]ethyl]cyclohexanone in 50 ml of tetrahydrofuran and 200 ml of tert.-butyl methyl ether and stirred at room temperature for a further 1 hour. Subsequently, the reaction mixture is suction filtered and the filtrate is concentrated. The crude product obtained is treated with 250 ml of hexane. The mixture is stirred at room temperature for 10 minutes and suction filtered. Concentration of the filtrate and purification of the product obtained by chromatography on silica gel with hexane and hexane/ethyl acetate finally gives 4-chloro-1-[trans-4-[2-(4-methoxymethlidene)cyclohexyl)ethyl]cyclohexyl]benzene.

f) A solution of 18.1 g of 4-chloro-1-[trans-4-{2-(4-methoxymethylidene)cyclohexyl)ethyl]cyclohexyl]-benzene in 90 ml of tetrahydrofuran is treated with 22.5 ml of 2N hydrochloric acid and boiled at reflux for 30 minutes while stirring and gassing with nitrogen. Subsequently, the reaction mixture is cooled to room temperature, poured into 400 ml of water and extracted with methylene chloride. The organic phases are washed with water, dried over sodium sulphate, filtered and concentrated. The residue is dissolved in 150 ml of tert.-butyl methyl ether. The solution is evaporated to a large extent and then treated with 200 ml of methanol. Crystallization at −25° C. and recrystallization of the colourless, crystalline precipitate gives pure trans-4-[2-(trans-4-(4-chlorophenyl)cyclohexyl)ethyl]cyclohexanecarboxaldehyde.

The following compounds can be prepared in an analogous manner:
trans-4-{2-[trans-4-(3,4-Difluorophenyl)cyclohexyl]ethyl}cyclohexanecarboxaldehyde,
trans-4-{2-[trans-4-(3-fluoro-4-chlorophenyl)cyclohexyl]ethyl}cyclohexanecarboxaldehyde,
trans-4-{2-[trans-4-(3,4-dichlorophenyl)cyclohexyl]ethyl}cyclohexanecarboxaldehyde.

EXAMPLE 5 a) A Grignard reagent solution prepared from 46.8 g of 1-bromo-3,4-difluorobenzene and 6 g of magnesium in 150 ml of tetrahydrofuran is added dropwise at −65° C. under nitrogen to a solution of 72.8 ml of triisopropyl borate in 200 ml of tetrahydrofuran. The mixture is stirred at −65° C. for 1 hour, warmed to 14°-20° C., treated dropwise with 100 ml of 10 percent (v/v) sulphuric acid, left to stand overnight and the separated salt is filtered off. The aqueous phase of the filtrate is separated and extracted with diethyl ether. The organic phases are combined, washed with sodium chloride solution, dried over sodium sulphate and evaporated. After boiling with hexane the residue gives 22.1 g of colourless 3,4-difluorophenylboric acid m.p. 275°-277.5° C. (sublimed).

b) A mixture of 6.2 g of 3,4-difluorophenylboric acid, 8.5 g of 2,5-dibromopyridine, 0.31 g of tetrakistriphenylphosphine palladium, 60 ml of ethanol, 120 ml of benzene and 120 ml of 2N sodium carbonate solution is heated to boiling (66° C.) for 7 hours while stirring. After cooling the mixture is extracted with diethyl ether. The organic phase is washed with 100 ml of saturated sodium hydrogen carbonate solution and 100 ml of water, dried over sodium sulphite, filtered and concentrated. Purification of the residue by chromatography on silica gel with hexane/ethyl acetate 19:1 yields pure 5-bromo-2-(3,4-difluorophenyl)pyridine.

c) A solution of 10.62 g of 4-chlorocyclohexanecarboxalde-hyde in 150 ml of toluene is treated with 11.5 ml of 1,3-propanediol and 1 g of Amberlyst ® 15 and heated to boiling for 2 hours on a water separator while stirring. The reaction mixture is treated with 2 ml of triethylamine and, after cooling, is filtered. The filtrate is washed three times with 30 ml of water, dried over sodium sulphate and concentrated. There is obtained 2-(4-chlorocyclohexyl)-1,3-dioxane.

d) A Grignard reagent prepared from 12.28 g of 2-(4-chlorocyclohexyl)-1,3-dioxane and 1.45 g of magnesium in 70 ml of diethyl ether is stirred at −78° C. for 30 minutes in a nitrogen atmosphere with 250 ml of tetrahydrofuran and 4.3 g of copper(I) bromide. Then, a solution of 4.06 g of 2-(4-chlorocyclohexyl)-1,3-dioxane (from step b) in 30 ml of tetrahydrofuran is added dropwise. The reaction mixture is stirred at −78° C. for a further 2 hours and overnight without the bath, treated dropwise with 20 ml of conc. ammonia and diluted with 50 ml of water. The aqueous phase is separated and extracted with 50 ml of diethyl ether. The combined organic phase is washed three times with 50 ml of sodium chloride solution each time, dried over sodium sulphate, filtered and concentrated. Chromatography of the residue on silica gel with hexane/ethyl acetate 9:1 yields 2-(3,4-difluorophenyl)-5-[4-(1,3-dioxan-2-yl)cyclohexyl]pyridine.

e) A mixture of 1.65 g of 2-(3,4-difluorophenyl)-5-[4-(1,3-dioxan-2-yl)cyclohexyl]pyridine, 15 ml of toluene and 10 ml of formic acid is stirred at room temperature for 10 hours and subsequently carefully neutralized to pH 7 with saturated sodium carbonate solution. The aqueous phase is separated and extracted twice with toluene, the organic phases are combined, washed with water, dried over sodium sulphate and evaporated. The residue is dissolved in 15 ml of methanol and added dropwise to 10 ml of 0.1N methanolic potassium hydroxide solution cooled to 0° C. The mixture is stirred at 0° C. for 1 hour, poured on to 40 ml of ice-water and extracted three times with 25 ml of diethyl ether each time. The organic phases are combined, washed neutral with water, dried over sodium sulphate and, after evaporation, give trans-4[2-(3,4-difluorophenyl)-5-pyridyl]-cyclohexanecarboxaldehyde (cis content about 8%).

The following compounds can be prepared analogously:
trans-4-[2-(3-Chloro-4-fluorophenyl)-5-pyridyl]cyclohexanecarboxaldehyde,
trans-4-[2-(4-chlorophenyl)-5-pyridyl]cyclohexanecarboxaldehyde,
trans-4-[2-(3,4-dichlorophenyl)-5-pyridyl]cyclohexanecarboxaldehyde, trans-4-[2-(4-chloro-3-fluorophenyl)-5-pyridyl]cyclohexanecarboxaldehyde.

EXAMPLE 6 a) A mixture of 85 g of 6-chloro-3-pyridinecarbinol, 800 ml of dioxan and 129.8 g of 3,4-dihydro-2H-pyran was treated with 5.7 g of p-toluenesulphonic acid monohydrate, stirred at room temperature for 0.75 hours and subsequently at 65° C. for 2.75 hours. The reaction mixture was treated with 15 ml of triethylamine and, after cooling, taken up in diethyl ether. Repeated washing with saturated sodium chloride solution, drying over sodium sulphate and evaporation yielded 153.2 g of crude 2-chloro-5-[(tetrahydro-2-pyranyloxy)methyl]pyridine as a brown-red oil.

b) A two-phase mixture of 5.7 g of 3,4-difluorophenylboric acid, 7.5 g of crude 2-chloro-5-[(tetrahydro-2-pyranyloxy)methyl]pyridine, 0.38 g of tetrakis(-triphenylphosphine)palladium, 60 ml of ethanol, 120 ml of benzene and 120 ml of 2N sodium carbonate solution was heated to boiling for 7 hours while stirring vigorously. After cooling the mixture was diluted with 200 ml of diethyl ether, the phases were separated and the organic phase was washed with 100 ml of saturated sodium hydrogen carbonate and 100 ml of water. The organic phase was extracted twice with 50 ml of 3N hydrochloric acid each time. The acidic-aqueous solution was left to stand for 45 minutes, made alkaline with dilute sodium hydroxide solution and the product was extracted with diethyl ether. The organic phase was washed neutral, dried over sodium sulphate and, after evaporation, yielded 6.1 g of solid, pure 6-(3,4-difluorophenyl)-3-pyridinecarbinol.

c) 0.3 ml of thionyl chloride was added dropwise to a solution of 0.5 g of 6-(3,4-difluorophenyl)-3-pyridinecarbinol in 20 ml of dichloromethane in an ice bath. The reaction mixture was stirred at 5° C. for 0.75 hour and at room temperature for 1.5 hours, then treated dropwise with 5 ml of saturated sodium carbonate solution. The aqueous phase (pH 8) was separated and extracted with dichloromethane. The combined organic phase was washed with water, dried over sodium sulphate and concentrated. There was obtained 0.46 g of pure 5-chloromethyl-2-(3,4-difluorophenyl)pyridine.

d) A mixture of 0.46 g of 5-chloromethyl-2-(3,4-difluorophenyl)pyridine, 0.6 g of triphenylphosphine and 10 ml of xylene was heated to boiling for 24 hours. After cooling the precipitate was filtered off, washed with toluene and dried. There was obtained 0.48 g of colourless [2-(3,4-difluorophenyl)-5-pyridyl]methyltriphenylphosphonium chloride, m.p. 259°-260.5° C.

e) A suspension of 12.05 g of [2-(3,4-difluorophenyl)-5-pyridyl]methyltriphenylphosphonium chloride in 70 ml of diethyl ether is treated with 2.67 g of potassium tert.-butylate in a nitrogen atmosphere. The dark yellow suspension is stirred at room temperature for a further 30 minutes. A solution of 2.74 g of -trans-4-formylcyclohexanecarbonitrile in 30 ml of diethyl ether is then added dropwise at 0° C. The reaction mixture is stirred at 0° C. for a further 1 hour, then stirred with 40 ml of 1N sodium hydrogen carbonate solution and diluted with diethyl ether. The organic phase is separated, washed neutral with water, dried over sodium sulphate and concentrated. The residue is chromatographed on silica gel with hexane/ethyl acetate 3:1 (v/v). There is obtained trans-4-[2-[2-(3,4-difluorophenyl)-5-pyridyl]vinyl]cyclohexanecarbonitrile.

f) A solution of 4.9 g of trans-4-[2-[2-(3,4-difluorophenyl)-5-pyridyl]vinyl]cyclohexanecarbonitrile in 120 ml of toluene is hydrogenated with 0.5 g of 10 percent palladium/carbon at room temperature and normal pressure. Filtration and evaporation of the filtrate yields trans-4-[2-[2-(3,4-difluorophenyl)-5-pyridyl]ethyl]cyclohexanecarbonitrile.

g) A solution of 4.8 g of trans-4-[2-[2-(3,4-difluorophenyl)-5-pyridyl]ethyl]cyclohexanecarbonitrile in 150 ml of toluene is treated at −78° C. under nitrogen with a solution of 24 ml of 1.2M diisobutylaluminium hydride in toluene. The reaction mixture is stirred at −78° C. for 1 hour and poured into 200 ml of saturated ammonium chloride solution. The aqueous phase is separated and washed twice with toluene. The organic phases are combined, washed with water, dried over sodium sulphate and evaporated. trans-4-[2-[2-(3,4-Difluorophenyl)-5-pyridyl]ethyl]cyclohexanecarbonitrile is obtained.

The following compounds can be prepared in an analogous manner:

trans-4-[2-(2-[4-Fluorophenyl]-5-pyridyl)ethyl]cyclohexanecarboxaldehyde, trans-4-[2-(2-[3-chloro-4-fluorophenyl]-5-pyridyl)ethyl]cyclohexanecarboxaldehyde, trans-4-[2-(2-[4-chlorophenyl]-5-pyridyl)ethyl]cyclohexanecarboxaldehyde, trans-4-[2-(2-[3,4-dichlorophenyl]-5-pyridyl)ethyl]cyclohexanecarboxaldehyde, trans-4-[2-(2-[4-chloro-3-fluorophenyl]-5-pyridyl)ethyl]cyclohexanecarboxaldehyde.

EXAMPLE 7

The pyrimidine compounds Ig and Ih can be manufactured in the following manner:

a) A suspension of 21 g of anhydrous (methoxymethyl)triphenylphosphonium chloride in 100 ml of abs. diethyl ether is treated with 6.86 g of potassium tert.-butylate at 0° C. in a nitrogen atmosphere. The red suspension is stirred at 0° C. for 15 minutes and then treated dropwise at 5°-10° C. with a solution of 7.9 g of trans-4-(1E-pentenyl)cyclohexanecarboxaldehyde in 30 ml of diethyl ether. The mixture is stirred at room temperature for 4 hours, washed with 40 ml of ice-cold saturated sodium hydrogen carbonate solution and twice with 50 ml of water each time, dried over sodium sulphate, filtered and concentrated. The residue is dissolved in 100 ml of hexane and 40 ml of 80 percent aqueous methanol. The hexane phase is washed with 10 ml of 80 percent aqueous methanol and 20 ml of water, dried over sodium sulphate and concentrated. Distillation of the residue in a vacuum yields trans-1-(2-methoxy-vinyl)-4-(1E-pentenyl)cyclohexane as a colourless oil.

b) 20 ml of trimethyl orthoformate are treated at 0°-5° C. in a nitrogen atmosphere with 0.38 ml of boron trifluoride diethyl etherate and then dropwise with 7.30 ml of trans-1-(2-methoxyvinyl)-4-(1E-pentenyl)cyclohexane. The reaction mixture is left to stand at 3° C. for 3 hours, treated with 0.38 ml of triethanolamine and concentrated in a vacuum. The residue is dissolved in 50 ml of hexane, the solution is washed with 10 ml of saturated sodium hydrogen carbonate solution and twice with 10 ml of water each time and concentrated. There is obtained [trans-4-(1E-pentenyl)cyclohexyl]-malonaldehyde tetramethyl acetal as a colourless oil.

c) A mixture of 8.9 g of [trans-4-(1E-pentenyl)cyclohexyl]malonaldehyde tetramethyl acetal, 0.67 ml of water and 0.08 g of p-toluenesulphonic acid monohydrate is heated to boiling for 1 hour, cooled, treated with 0.22 g of sodium hydrogen carbonate and stirred for 15 minutes. The suspension is filtered and the residue is washed with methanol. In the meanwhile, a sodium methylate solution is prepared from 1.06 g of sodium and 45 ml of methanol. This solution is treated firstly with 6.06 g of p-chlorobenzamidine hydrochloride and subsequently within 20 minutes with the above 3-methoxy-2-[trans-4-(1E-pentenyl]-cyclohexyl]acrolein solution.

The mixture is stirred for 18 hours, neutralized to pH 5 with 2.5 ml of 25 percent hydrochloric acid and cooled to −20° C. The suspension is suction filtered, the residue is washed with methanol (−20° C.), the filterates are combined, dried and concentrated. The evaporation residue is taken up in diethyl ether, washed with water, dried and evaporated. After recrystallization from ethyl acetate the residue gives analytically pure 2-(4-chlorophenyl)-5-[trans-4-(1E-pentenyl)cyclohexyl]pyrimidine.

In an analogous manner there can be prepared:

2-(3,4-Difluorophenyl)-5-(trans-4-vinylcyclohexyl)-pyrimidine, m.p. (C-N) 96.0° C., cl.p. (N-I) 109.8° C., 2-(4-chloro-3-fluorophenyl)-5-(trans-4-vinylcyclohexyl)pyrimidine, 2-(3-chloro-4-fluorophenyl)-5-(trans-4-vinylcyclohexyl)pyrimidine, 2-(4-chlorophenyl)-5-(trans-4-vinylcyclohexyl)-pyrimidine, m.p. (C-N) 129.7° C., cl.p. (N-I) 178.5° C., 2-(3,4-dichlorophenyl)-5-(trans-4-vinylcyclohexyl)-pyrimidine, 2-(3,4-difluorophenyl)-5-(trans-4-(1E-propenyl)cyclohexyl]pyrimidine, 2-(4-chloro-3-fluorophenyl)-5-(trans-4-(1E-propenyl)cyclohexyl]pyrimidine, 2-(3-chloro-4-fluorophenyl)-5-(trans-4-(1E-propenyl)cyclohexyl]pyrimidine, 2-(4-chlorophenyl)-5-(trans-4-(1E-propenyl)cyclohexyl]pyrimidine, 2-(3,4-dichlorophenyl)-5-(trans-4-(1E-propenyl)cyclohexyl]pyrimidine, 2-(3,4-difluorophenyl)-5-(trans-4-(1E-butenyl)cyclohexyl]pyrimidine, 2-(4-chloro-3-fluorophenyl)-5-(trans-4-(1E-butenyl)cyclohexyl]pyrimidine, 2-(3-chloro-4-fluorophenyl)-5-(trans-4-(1E-butenyl)cyclohexyl]pyrimidine, 2-(4-chlorophenyl)-5-(trans-4-(1E-butenyl)cyclohexyl]pyrimidine, 2-(3,4-dichlorophenyl)-5-(trans-4-(1E-butenyl)cyclohexyl]pyrimidine, 2-(3,4-difluorophenyl)-5-(trans-4-(1E-pentenyl)cyclohexyl]pyrimidine, 2-(4-chloro-3-fluorophenyl)-5-(trans-4-(1E-pentenyl)cyclohexyl]pyrimidine, 2-(3-chloro-4-fluorophenyl)-5-(trans-4-(1E-pentenyl)cyclohexyl]pyrimidine, 2-(3,4-dichlorophenyl)-5-(trans-4-(1E-pentenyl)cyclohexyl]pyrimidine, 2-(3,4-difluorophenyl)-5-{2-[trans-4-(vinyl)cyclohexyl]ether}pyrimidine, 2-(4-chloro-3-fluorophenyl)-5-{2-[trans-4-(vinyl)cyclohexyl]ether}pyrimidine, 2-(3-chloro-4-fluorophenyl)-5-{2-[trans-4-(vinyl)cyclohexyl]ether}pyrimidine, 2-(4-chlorophenyl)-5-{2-[trans-4-(vinyl)cyclohexyl]ethyl}pyrimidine, m.p. (C-N) 109.9° C., cl.p. (N-I) 144.4° C., 2-(3,4-dichlorophenyl)-5-{2-[trans-4-(vinyl)cyclohexyl]ethyl}pyrimidine, 2-(3,4-difluorophenyl)-5-{2-[trans-4-(1E-propenyl)cyclohexyl]ethyl}pyrimidine, 2-(4-chloro-3-fluorophenyl)-5-{2-[trans-4-(1E-propenyl)cyclohexyl]ethyl}pyrimidine, 2-(3-chloro-4-fluorophenyl)-5-{2-[trans-4-(1E-propenyl)cyclohexyl]ethyl}pyrimidine, 2-(4-chlorophenyl)-5-{2-[trans-4-(1E-propenyl)cyclohexyl]ethyl}pyrimidine, 2-(3,4-dichlorophenyl)-5-{2-[trans-4-(1E-propenyl)cyclohexyl]ethyl}pyrimidine, 2-(3,4-difluorophenyl)-5-{2-[trans-4-(1E-butenyl)cyclohexyl]ethyl}pyrimidine, 2-(4-chloro-3-fluorophenyl)-5-{2-[trans-4-(1E-butenyl)cyclohexyl]ethyl}pyrimidine, 2-(3-chloro-4-fluorophenyl)-5-{2-[trans-4-(1E-butenyl)cyclohexyl]ethyl}pyrimidine, 2-(4-chlorophenyl)-5-{2-[trans-4-(1E-butenyl)cyclohexyl]ethyl}pyrimidine, 2-(3,4-dichlorophenyl)-5-{2-[trans-4-(1E-butenyl)cyclohexyl]ethyl}pyrimidine, 2-(3,4-difluorophenyl)-5-{2-[trans-4-(1E-pentenyl)cyclohexyl]ethyl}pyrimidine, 2-(4-chloro-3-fluorophenyl)-5-{2-[trans-4-(1E-pentenyl)cyclohexyl]ethyl}pyrimidine, 2-(3-chloro-4-fluorophenyl)-5-{2-[trans-4-(1E-pentenyl)cyclohexyl]ethyl}pyrimidine, 2-(4-chlorophenyl)-5-{2-[trans-4-(1E-pentenyl)cyclohexyl]ethyl}pyrimidine, 2-(3,4-dichlorophenyl)-5-{2-[trans-4-(1E-pentenyl)cyclohexyl]ethyl}pyrimidine.

EXAMPLE 8

Binary mixtures with 4-(trans-4-penylcyclohexyl)-benzo-nitrile were prepared in order to investigate the properties of the compounds of formula I in mixtures. The threshold potential and the response times were measured in a TN cell (low bias tilt) having a plate separation of 8 μm; the 2.5-fold value of the threshold potential being chosen as the operating voltage. The corresponding data for pure 4-(trans-4-penylcyclohexyl)benzonitrile are: cl.p. (N-I) 54.6° C., $V_{10}=1.62$ V, $t_{on}=30$ ms, $t_{off}=42$ ms, $\Delta n=0.120$.

Mixture A 90 wt. % of 4-(trans-4-pentylcyclohexyl)benzonitrile,
10 wt. % of 4-[trans-4-vinylcyclohexyl]-3',4'-difluorobiphenyl,
cl.p. (N—I) 55.2° C., $V_{10}=1.42$ V, $t_{on}=29$ ms, $t_{off}=42$ ms, $\Delta n=0.124$.

Mixture B 80 wt. % of 4-(trans-4-pentylcyclohexyl)benzonitrile,
20 wt. % of 4-[trans-4-vinylcyclohexyl]-3',4'-difluorobiphenyl,
cl.p. (N—I) 55.8° C., $V_{10}=1.35$ V, $t_{on}=33$ ms, $t_{off}=46$ ms, $\Delta n=0.126$.

Mixture C 90 wt. % of 4-(trans-4-pentylcyclohexyl)benzonitrile,
10 wt. % of 4-[trans-4-(1E-propenyl)cyclohexyl]-3',4'-difluorobiphenyl
cl.p. (N—I) 57.8° C., $V_{10}=1.49$ V, $t_{on}=25$ ms, $t_{off}=41$ ms, $\Delta n=0.126$.

Mixture D 80 wt. % of 4-(trans-4-pentylcyclohexyl)benzonitrile,
20 wt. % of 4-[trans-4-(1E-propenyl)cyclohexyl]-3',4'-difluorobiphenyl
cl.p. (N—I) 61.1° C., $V_{10}=1.51$ V, $t_{on}=26$ ms, $t_{off}=42$ ms, $\Delta n=0.129$.

-continued

Mixture E
90 wt. % of 4-(trans-4-pentylcyclohexyl)benzonitrile,
10 wt. % of 4-[trans-4-(1E-butenyl)cyclohexyl]-3',4'-difluorobiphenyl
cl.p. (N—I) 56.6° C., $V_{10}$ = 1.56 V, $t_{on}$ = 25 ms, $t_{off}$ = 44 ms, $\Delta n$ = 0.125.

Mixture F
80 wt. % of 4-(trans-4-pentylcyclohexyl)benzonitrile,
20 wt. % of 4-[trans-4-(1E-butenyl)cyclohexyl]-3',4'-difluorobiphenyl
cl.p. (N—I) 58.9° C., $V_{10}$ = 1.61 V, $t_{on}$ = 26 ms, $t_{off}$ = 45 ms, $\Delta n$ = 0.127.

Mixture G
90 wt. % of 4-(trans-4-pentylcyclohexyl)benzonitrile,
10 wt. % of 4-[trans-4-(1E-pentenyl)cyclohexyl]-3',4'-difluorobiphenyl
cl.p. (N—I) 56.8° C., $V_{10}$ = 1.62 V, $t_{on}$ = 25 ms, $t_{off}$ = 42 ms, $\Delta n$ = 0.122.

Mixture H
80 wt. % of 4-(trans-4-pentylcyclohexyl)benzonitrile,
20 wt. % of 4-[trans-4-(1E-pentenyl)cyclohexyl]-3',4'-difluorobiphenyl
cl.p. (N—I) 60.8° C., $V_{10}$ = 1.60 V, $t_{on}$ = 29 ms, $t_{off}$ = 49 ms, $\Delta n$ = 0.124.

Mixture I
90 wt. % of 4-(trans-4-pentylcyclohexyl)benzonitrile,
10 wt. % of 4-(trans-4-(vinylcyclohexyl)-4'-chloro-3'-fluorobiphenyl
cl.p. (N—I) 58.1° C., $V_{10}$ = 1.65 V, $t_{on}$ = 25 ms, $t_{off}$ = 43 ms, $\Delta n$ = 0.130.

Mixture J
80 wt. % of 4-(trans-4-pentylcyclohexyl)benzonitrile,
20 wt. % of 4-(trans-4-vinylcyclohexyl)-4'-chloro-3'-fluorobiphenyl
cl.p. (N—I) 62.1° C., $V_{10}$ = 1.66 V, $t_{on}$ = 26 ms, $t_{off}$ = 42 ms, $\Delta n$ = 0.134.

Mixture K
90 wt. % of 4-(trans-4-pentylcyclohexyl)benzonitrile,
10 wt. % of 4-[trans-4-(1E-propenyl)cyclohexyl]-4'-chloro-3'-fluorobiphenyl
cl.p. (N—I) 60.6° C., $V_{10}$ = 1.68 V, $t_{on}$ = 25 ms, $t_{off}$ = 43 ms, $\Delta n$ = 0.131.

Mixture L
80 wt. % of 4-(trans-4-pentylcyclohexyl)benzonitrile,
20 wt. % of 4-[trans-4-(1E-propenyl)cyclohexyl]-4'-chloro-3'-fluorobiphenyl
cl.p. (N—I) 68.7° C., $V_{10}$ = 1.78 V, $t_{on}$ = 26 ms, $t_{off}$ = 45 ms, $\Delta n$ = 0.137.

Mixture M
90 wt. % of 4-(trans-4-pentylcyclohexyl)benzonitrile,
10 wt. % of 4-[trans-4-(1E-butenyl)cyclohexyl]-4'-chloro-3'-fluorobiphenyl
cl.p. (N—I) 59.4° C., $V_{10}$ = 1.63 V, $t_{on}$ = 26 ms, $t_{off}$ = 43 ms, $\Delta n$ = 0.129.

Mixture N
80 wt. % of 4-(trans-4-pentylcyclohexyl)benzonitrile,
20 wt. % of 4-[trans-4-(1E-butenyl)cyclohexyl]-4'-chloro-3'-fluorobiphenyl
cl.p. (N—I) 63.7° C., $V_{10}$ = 1.66 V, $t_{on}$ = 27 ms, $t_{off}$ = 44 ms, $\Delta n$ = 0.138.

Mixture O
90 wt. % of 4-(trans-4-pentylcyclohexyl)benzonitrile,
10 wt. % of 4-[trans-4-(1E-pentenyl)cyclohexyl]-4'-chloro-3'-fluorobiphenyl
cl.p. (N—I) 59.8° C., $V_{10}$ = 1.65 V, $t_{on}$ = 25 ms, $t_{off}$ = 42 ms, $\Delta n$ = 0.127.

Mixture P
80 wt. % of 4-(trans-4-pentylcyclohexyl)benzonitrile,
20 wt. % of 4-[trans-4-(1E-pentenyl)cyclohexyl]-4'-chloro-3'-fluorobiphenyl
cl.p. (N—I) 63.4° C., $V_{10}$ = 1.72 V, $t_{on}$ = 25 ms, $t_{off}$ = 43 ms, $\Delta n$ = 0.134.

Mixture Q
90 wt. % of 4-(trans-4-pentylcyclohexyl)benzonitrile,
10 wt. % of 4-(trans-4-vinylcyclohexyl)-4'-chlorobiphenyl
cl.p. (N—I) 61.4° C., $V_{10}$ = 1.71 V, $t_{on}$ = 23 ms, $t_{off}$ = 39 ms, $\Delta n$ = 0.132.

Mixture R
80 wt. % of 4-(trans-4-pentylcyclohexyl)benzonitrile,
20 wt. % of 4-(trans-4-vinylcyclohexyl)-4'-chlorobiphenyl
cl.p. (N—I) 67.1° C., $V_{10}$ = 1.78 V, $t_{on}$ = 24 ms, $t_{off}$ = 40 ms, $\Delta n$ = 0.131.

Mixture S
90 wt. % of 4-(trans-4-pentylcyclohexyl)benzonitrile,
10 wt. % of 4-[trans-4-(1E-pentenyl)cyclohexyl]-4'-chlorobiphenyl
cl.p. (N—I) 60.7° C., $V_{10}$ = 1.69 V, $t_{on}$ = 25 ms, $t_{off}$ = 41 ms, $\Delta n$ = 0.130.

Mixture T
90 wt. % of 4-(trans-4-pentylcyclohexyl)benzonitrile,
10 wt. % of 5-[2-(trans-4-vinylcyclohexyl)ethyl]-2-(3,4-difluorophenyl)pyridine
cl.p. (N—I) 52.3° C., $V_{10}$ = 1.48 V, $t_{on}$ = 30 ms, $t_{off}$ = 45 ms, $\Delta n$ = 0.124.

Mixture U
90 wt. % of 4-(trans-4-pentylcyclohexyl)benzonitrile,
10 wt. % of 5-[2-[trans-4-(1E-propenyl)cyclohexyl]ethyl]-2-(3,4-difluorophenyl)pyridine
cl.p. (N—I) 57.1° C., $V_{10}$ = 1.63 V, $t_{on}$ = 26 ms, $t_{off}$ = 44 ms, $\Delta n$ = 0.125.

Mixture V
80 wt. % of 4-(trans-4-pentylcyclohexyl)benzonitrile,
20 wt. % of 5-[2-[trans-4-(1E-propenyl)cyclohexyl]ethyl]-2-(3,4-difluorophenyl)pyridine
cl.p. (N—I) 60.2° C., $V_{10}$ = 1.59 V, $t_{on}$ = 30 ms, $t_{off}$ = 49 ms, $\Delta n$ = 0.130.

What is claimed is:

1. A compound of the formula

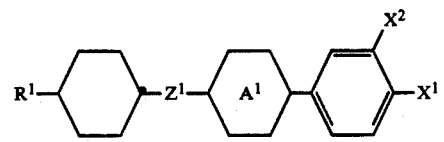

wherein $R^1$ is 1E-alkenyl of 2 to 12 carbon atoms; $Z^1$ is a single covalent bond or —CH$_2$CH$_2$—; ring $A^1$ is 1,4-phenylene, pyrimidin-2,5-diyl, pyridin-2,5-diyl or, when $Z^1$ is —CH$_2$CH$_2$—, $A^1$ also can be trans-1,4-cyclohexylene; $X^1$ is fluorine or chlorine; and $X^2$ is fluorine or chlorine; or when $X^1$ is chlorine, $X^2$ also can be hydrogen; and when ring $A^1$ is pyridin-2,5-diyl and $Z^1$ is —CH$_2$CH$_2$—, $X^2$ also can be hydrogen.

2. Compounds of the general formula

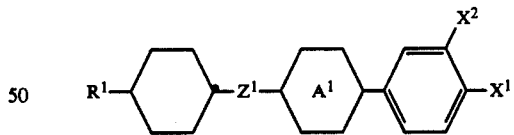

wherein $Z^1$ denotes a single covalent bond or —CH$_2$—CH$_2$—; ring $A^1$ represents 1,4-phenylene, pyrimidine-2,5-diyl, pyridine-2,5-diyl or, when $Z^1$ stands for —CH$_2$—CH$_2$—, also trans-1,4-cyclohexylene; $X^1$ stands for fluorine or chlorine; $X^2$ signifies fluorine, chlorine or, when $X^1$ stands for chlorine, also hydrogen; and $R^1$ signifies 1E-alkenyl with 2 to 12 carbon atoms.

3. A compound according to claim 1, selected from the group of compounds of the formulae

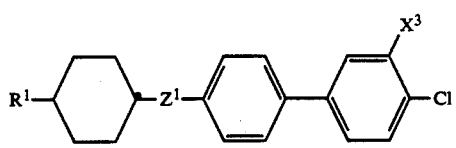

-continued

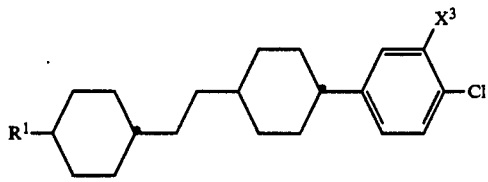

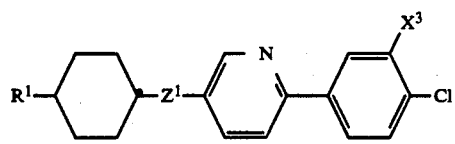

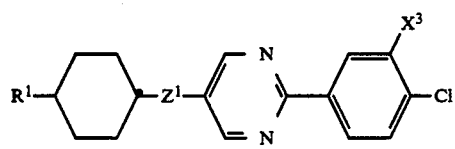

wherein $R^1$ is a 1E-alkenyl with 2 to 12 carbon atoms; $Z^1$ is a single covalent bond or —CH$_2$CH$_2$; and $X^3$ is hydrogen, chlorine or fluorine.

4. A compound according to claim 3, wherein $Z^1$ is a single covalent bond.

5. A compound according to claim 1 selected from the group of compounds of the formulas

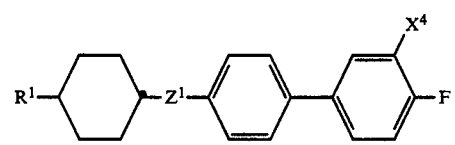

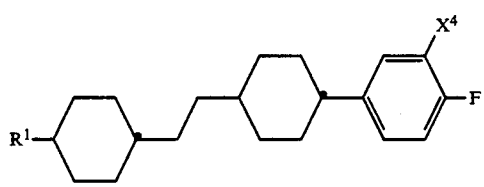

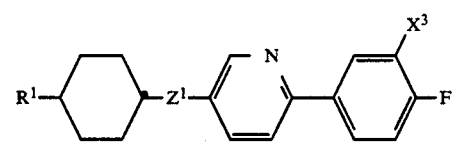

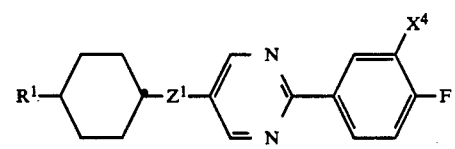

wherein $R^1$ is 1E-alkenyl with 2 to 12 carbon atoms; $Z^1$ is a single covalent bond or —CH$_2$CH$_2$—; and $X^4$ is chlorine or fluorine.

6. A compound according to claim 1, wherein ring $A^1$ is pyridin-2,5-diyl, and $X^1$ is chlorine.

7. A compound according to claim 1, wherein $R^1$ is a straight-chain residue.

8. A compound according to claim 1, wherein $R^1$ has 2 to 7 carbon atoms.

9. A liquid crystalline mixture having at least two components, wherein at least one component is a compound of the formula

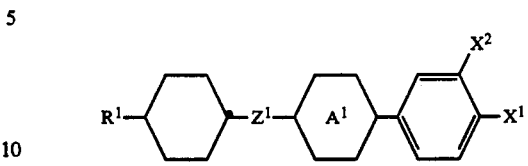

wherein $R^1$ is 1E-alkenyl of 2 to 12 carbon atoms; $Z^1$ is a single covalent bond or —CH$_2$CH$_2$—; ring $A^1$ is 1,4-phenylene, pyrimidin-2,5-diyl, pyridin-2,5-diyl or, when $Z^1$ is —CH$_2$CH$_2$—, $A^1$ also can be trans-1,4-cyclohexylene; $X^1$ is fluorine or chlorine; and $X^2$ is fluorine or chlorine; or when $X^1$ is chlorine, $X^2$ also can be hydrogen; and when ring $A^1$ is pyridin-2,5-diyl and $Z^1$ is —CH$_2$CH$_2$—, $X^2$ also can be hydrogen.

10. The liquid crystalline mixture according to claim 9, wherein the content of said at least one component is about 1–50 weight percent.

11. The liquid crystalline mixture according to claim 9, comprising at least one compound of formula I and at least one compound selected from the group of compounds of the formulae

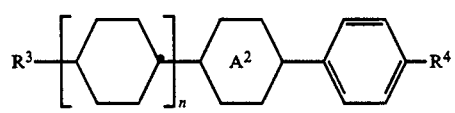

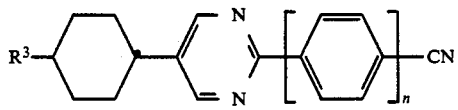

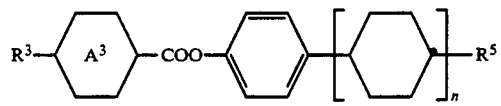

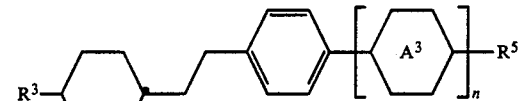

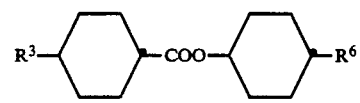

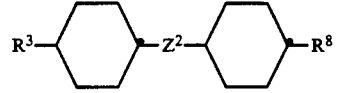

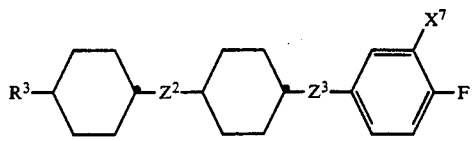

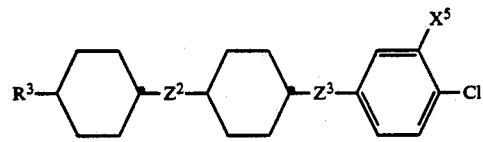
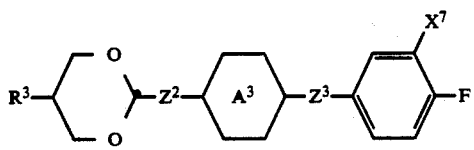
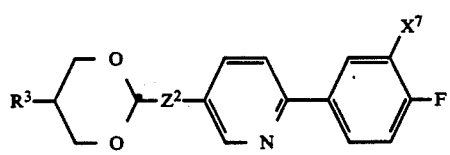
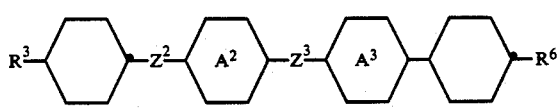
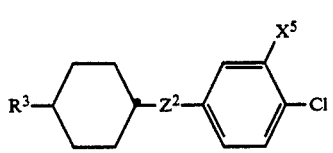
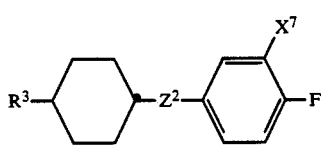
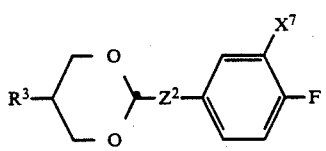
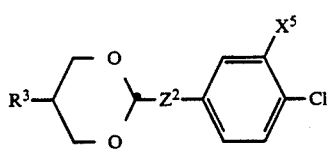
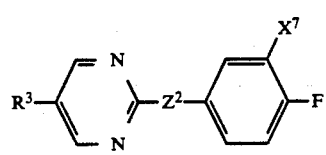
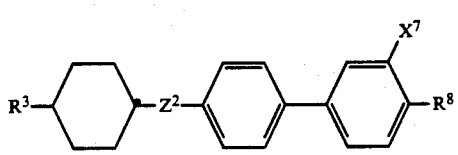
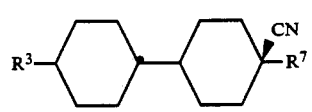

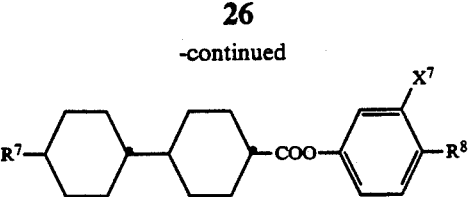
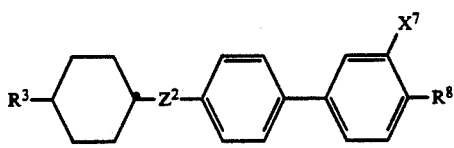

wherein n is either 0 or 1; $R^3$ and $R^6$ each independently are alkyl, 3E-alkenyl, 4-alkenyl, alkoxyalkyl or, when $R^3$ or $R^6$ are bonded to either trans-1,4-cyclohexylane or trans-1,3-dioxane-2,5-diyl, $R^3$ and $R^6$ also can be also 1E-alkenyl; ring $A^2$ is 1,4-phenylene, trans-1,4-cyclohexylene, pyridine-2,5-diyl, pyrimidine-2,5-diyl or trans-1,3-dioxane-2,5-diyl; $R^4$ is cyano, -NCS, fluorine, alkyl, 3E-alkenyl, 4-alkenyl, alkoxy, 2E-alkenyloxy, 3-alkenyloxy or 1-alkynyl; ring $A^3$ is 1,4-phenylene or trans-1,4-cyclohexylene; $R^5$ is alkyl, 3E-alkenyl-4-alkenyl, when bonded to a trans-1,4-cyclohexylene ring, $R^5$ also can be 1E-alkenyl or, when bonded to a trans-1,4-cyclohexylene ring, $R^5$ also can be 1E-alkenyl or, when $R^5$ is bonded to a 1,4-phenylene ring, $R^5$ also can be cyano, -NCS, alkoxy, 2E-alkenyloxy or 3-alkenyloxy; $R^7$ is alkyl, 1E-alkenyl, 3E-alkenyl or 4-alkenyl; $Z^2$ and $Z^3$ each individually are a single covalent bond or $-CH_2CH_2-$, with the proviso that two aromatic rings are always linked by a single covalent bond; $R^8$ is cyano, alkyl, 3E-alkenyl, 4-alkenyl, alkoxy, 2E-alkenyloxy, 3-alkenyloxy, alkoxymethyl, (2E-alkenyl)oxymethyl or when bonded to a trans-1,4-cyclohexylene ring, $R^8$ is also 1E-alkenyl; $X^5$ is hydrogen, chlorine or fluorine; $X^6$ is cyano, chlorine or fluorine; and $X^7$ is hydrogen or fluorine.

12. An electro-optical cell comprising:
(a) two plate means;
(b) liquid crystal means disposed between the two plate means and including a compound of the formula:

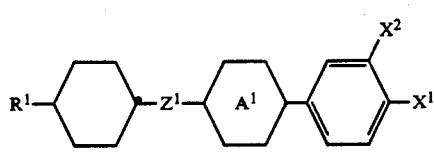

wherein $R^1$ is 1E-alkenyl of 2 to 12 carbon atoms; $Z^1$ is a single covalent bond or $-CH_2CH_2-$; ring $A^1$ is 1,4-phenylene, pyrimidin-2,5-diyl, pyridin-2,5-diyl or, when $Z^1$ is $-CH_2CH_2-$, $A^1$ also can be trans-1,4-cyclohexylene; $X^1$ is fluorine or chlorine; and $X^2$ is fluorine or chlorine; or when $X^1$ is chlorine, $X^2$ also can be hydrogen, and when ring $A^1$ is pyridin-2,5-diyl and $Z^1$ is $-CH_2CH_2-$, $X^2$ also can be hydrogen; and
(c) means for applying an electric potential to said plate means.

13. The compound of claim 1, 4-(trans-4-vinylcyclohexyl)-3',4'-difluorobiphenyl.

14. The compound of claim 1, 4-[trans-4-(1E-propenyl)cyclohexyl]-3',4'-difluorobiphenyl.

15. The compound of claim 1, 4-[trans-4-(1E-butenyl)cyclohexyl]-3',4'-difluorobiphenyl.

16. The compound of claim 1, 4-[trans-4-(1E-propenyl)cyclohexyl]-4'-chlorobiphenyl.

* * * * *